United States Patent [19]

Stolle et al.

[11] Patent Number: 4,897,265

[45] Date of Patent: Jan. 30, 1990

[54] METHOD FOR TREATING DISORDERS OF THE VASCULAR AND PULMONARY SYSTEMS

[75] Inventors: Ralph J. Stolle, Oregonia, Ohio; Lee R. Beck, Birmingham, Ala.

[73] Assignee: Stolle Research & Development Corporation, Cincinnati, Ohio

[21] Appl. No.: 1,848

[22] Filed: Jan. 9, 1987

Related U.S. Application Data

[60] Division of Ser. No. 546,162, Oct. 27, 1983, Pat. No. 4,636,384, which is a continuation-in-part of Ser. No. 384,625, Jun. 3, 1982, abandoned.

[51] Int. Cl.$^4$ .................. A61K 39/40; A61K 35/20
[52] U.S. Cl. .................. 424/87; 424/85.8
[58] Field of Search .................. 424/85, 85.8, 87

[56] References Cited

U.S. PATENT DOCUMENTS

| | | | |
|---|---|---|---|
| 3,128,230 | 4/1964 | Heinbach | 424/85 |
| 3,376,198 | 4/1968 | Petersen et al. | 424/85 |
| 3,911,108 | 10/1975 | Singh | 424/86 |
| 4,284,623 | 8/1981 | Beck | 424/85 |
| 4,324,782 | 4/1982 | Beck | 424/87 |
| 4,377,569 | 3/1983 | Phymate | 424/85 |
| 4,636,384 | 1/1987 | Stolle et al. | 424/87 |
| 4,732,757 | 3/1988 | Stolle et al. | 424/87 |

FOREIGN PATENT DOCUMENTS

| | | |
|---|---|---|
| 587849 | 12/1959 | Canada . |
| 1211876 | 11/1968 | United Kingdom . |
| 1505513 | 3/1978 | United Kingdom . |

OTHER PUBLICATIONS

Lascelles, Dairy Science Abstracts, vol. 25, pp. 359–364, 1963.
T. Kreofsky et al., *FASEB J.*, 2:A1607 (1988).
Unanue, E. R. et al., *Science*, 236:551–557 (1987).

*Primary Examiner*—Blondel Hazel
*Attorney, Agent, or Firm*—Saidman, Sterne, Kessler & Goldstein

[57] ABSTRACT

A method for treating vascular disorders or pulmonary disorders associated with smoking in an animal which comprises: administering to the animal milk collected from a bovid being maintained in a hyperimmune state, in an amount and for a time sufficient to produce anti arteriosclerotic or antiaging vascular effects or sparing effects on lung tissue.

13 Claims, 8 Drawing Sheets

METHOD FOR TREATING DISORDERS OF THE VASCULAR AND PULMONARY SYSTEMS

This is a division of application Ser. No. 546,162 filed Oct. 27, 1983, now U.S. Pat. No. 4,636,384 which is a Continuation-in-Part of application Ser. No. 384,625, filed June 3, 1982, now abandoned.

BACKGROUND OF THE INVENTION

1. Field of the Invention:

The present invention relates to a method for the treatment of disorders of the vascular and pulmonary systems, such as vascular aging and arteriosclerosis and disorders of the lungs associated with smoking.

2. Description of the Prior Art:

The normal vascular system of mammals, especially humans, includes all of the organs, such as the heart and the arteries, involved in blood transport and circulation. Two major disorders affect the vascular system in animals: arteriosclerosis and aging. Arteriosclerosis, a generic term for the thickening and hardening of the arterial wall, is responsible for the majority of deaths in the United States and most Westernized societies. There are various types of arteriosclerosis such as atherosclerosis, focal calcification, and arteriolosclerosis. The changes associated with arteriosclerosis (of the various types) and aging are partly overlapping. (See for example Harrison's "Principles of Internal Medicine," 9th Edition, pp. 156–1166.)

The normal artery wall consists of three reasonably well defined layers: the intima, the media and the adventitia. The intima is a layer of endothelial cells lining the lumen of all arteries. The endothelial cells are attached to each other by a series of junctional complexes and also are attached to an underlying meshwork of loose connective tissue, the basal lamina. The lining endothelial cells form a barrier that controls the entry of substances from the blood into the arterial wall. The media consists of smooth muscle cells arranged in either single layers or multiple layers. The outermost layer of the artery is the adventitia which is delimited by the external elastic lamina. This external coat consists of a loose interwoven mixture of thick bundles of collagen, elastic fibers of varying size and a mixture of smooth muscle cells and fibroblasts.

Maintenance of the endothelial cell lining is critical. Endothelial cell turnover occurs at a slow rate but may accelerate in focal areas by changing patterns of flow along the vessel wall. Intact endothelial cells function to prevent clotting partly by elaboration of prostacyclin that inhibits platelet function, thereby enhancing unimpeded flow of blood. When the lining is damaged, however, platelets adhere to it in part as the result of production of a different class of prostaglandins, the thromboxanes, and form a clot. The ability of the arterial wall to maintain the integrity of its endothelium, prevent platelet aggregation and insure the nutrition of its middle portion may be the critical determinants of the arteriosclerotic process.

The major change that occurs with normal aging in the arterial wall is a slow symmetrical increase in the thickness of the intima. This results from an accumulation of small muscle cells. In the nondiseased artery wall the lipid content, mainly cholesterol ester and phospholipid, also progressively increases with age. While most of the phospholipid in the normal artery wall appears to be derived from in situ synthesis, the cholesterol ester that accumulates with aging appears to be derived from plasma since it contains principally linoleic acid, the major plasma cholesterol ester of fatty acid. As the normal artery ages, smooth muscle cells and connective tissue accumulate in the intima, leading to progressive thickening of the layer coupled with progressive accumulation of fatty acid, resulting in a gradual increase in the rigidity of the vessels. The larger arteries may become dilated, elongated and porous and aneurysms may form in areas of encroaching degenerating arteriosclerotic plaque.

By far, the leading cause of death in the United States both above and below age 65 is atherosclerosis, the atheromatous form of arteriosclerosis. The lesions are commonly classifed as fatty streaks, fibrous plaques and complicated lesions. The fatty streaks are characterized by an accumulation of lipid-filled smooth muscle cells and fibrous tissue in focal areas of the intima, and are stained distinctively by fat soluble dyes. The lipid is mainly cholesterol oleate. Fibrous plaques are elevated areas of intima thickening and will present the most characteristic lesion of advancing arteriosclerosis. They appear in the abdominal aorta, coronary arteries and carotid arteries in the third decade and increase progressively with age. Complicated lesions are calcified fibrous plaques containing various degrees of necrosis, thrombosis and ulceration.

A number of factors called "risk factors" have been identified in individuals who develop atherosclerosis. The risk factor concept implies that a person with at least one risk factor is more likely to develop a clinical atherosclerotic event and to do so earlier than a person with no risk factors. The presence of multiple risk factors further accelerates atherosclerosis. Among the reversible or partially reversible risk factors are hyperlipidemia (hypercholesrerolemia and/or hypertriglyceridemia), hyperglycemia and diabetes, low levels of high density lipoproteins, hypertension, obesity, and cigarette smoking.

As stated in Harrison's, supra (p 1166), although the emergence of clinical consequences of atherosclerosis can be lessened, no convincing instance of regression or interruption of progression of atherosclerosis by removal or reversal of any single or group of risk factors has yet been proved in humans. The trend toward lower smoking, lower cholesterol and fat consumption and towards reduction of overweight and exercise programs has been helpful. Prevention rather than treatment, however, is the goal of public health professionals. An effective program of prophylaxis has not yet been established, although enough is known to guide in both identification and high risk and development of measures to reduce the risk.

Among the risk factors referred to above that might be particularly well suited to therapeutic treatment is hyperlipidemia. Although control of factors such as obesity and cigarette consumption depend, to a great degree, on the will and inclination of the individual, if a reasonable method for lowering, e.g., serum cholesterol, low density lipids (LDL) and triglyceride blood stream levels were provided, it would be suitable for treatment of a broad spectrum of individuals.

Because of the widespread distribution of vascular disorders such as arteriosclerosis disorders and the naturally occurring aging of the vascular system and its accompanying problems, a need exists for an effective method for both preventing and possibly treating these disorders.

If a natural food product, such as milk for example, could be obtained having anti-arteriosclerotic and aging effects it would be an easily administerable, readily available, safe therapeutic composition.

Another major system of mammals, especially humans, which is characterized by the progressive degeneration of the cells of the organs constituting that system, is the pulmonary system, and in particular, the lungs and associated bronchii and alveoli. Like arteriosclerosis and vascular aging, certain pulmonary disorders, including a general breakdown of the pulmonary system, short windedness and a decrease in the efficiency of the respiration is associated with and due to environmental irritants and pollutants, such as those contained in cigarette smoke.

It is known that prolonged smoking induces the accumulatin of deposits of carbon and other substances on and in the lungs, which destroy the respiratory function of the associated area. Similarly, smoking, and/or the presence of these deposits substantially increases the number of neutrophilis and lymphocytes present in mammalian lungs, both types of cells producing substances that are injurious to lung tissue.

As with arteriosclerosis, there has been some containment or alleviation of the disorders associated with smoking due to a reduction in the frequency of smoking in most age groups. However, in certain segments of the population, most notably teen age and young women, smoking has increased, multiplying the frequency of occurrence of disorders associated with smoking both in the current population and importantly in the foreseeable future.

As with cardiovascular diseases, treatment based on avoidance of pollutants such as smoking will have varying success, depending on the individual. But, if a method for reducing the amount of deposited matter could be found, such as stimulation of lung macrophage activity, a treatment of benefit to most individuals could be developed.

As with arteriosclerotic and vascular diseases in general, if a natural food product, such as milk for example could be obtained having a sparing effect on lungs exposed to smoke and the associated disorders, it would be an easily administerable, readily available, safe therapeutic composition.

It has been known in the prior art to produce milks having a variety of therapeutic effects. Beck, for example, has disclosed a milk containing antibody to Streptococcus mutans which has dental caries inhibiting effects (Beck, U.S. Pat. No. 4,324,782). The milk is obtained by immunizing a cow with *S. mutans* antigen in two stages and obtaining the therapeutic milk therefrom. Beck has also described a milk having antiarthritic properties U.S. Pat. No. 4,732,757, and has described and patented a milk having anti-inflammatory properties (U.S. Pat. No. 4,284,623). Heinbach, U.S. Pat. No. 3,128,230, has described milk containing globulins of α, β, γ components, by innoculating a cow with antigenic mixtures. Petersen (U.S. Pat. No. 3,376,198 and Canadian Pat. No. 587,849), Holm, U.S. Application (published) Ser. No. 628,987 and Tunnah et al (British Pat. No. 1,211,876) have also described antibody-containing milks.

None of the aforementioned references, however, disclose or suggest milk having antiarteriosclerotic or vascular anti aging properties or a sparing effect on lungs exposed to smoke.

SUMMARY OF THE INVENTION

It is therefore an object of the invention to provide milk having beneficial properties towards disorders of the vascular and pulmonary system.

Another object of the invention is to provide a process for producing such milk.

A further object of the invention is to provide a method for treating vascular disorders in animals.

A further object of the invention is to provide a method for testing disorders in animals associated with the exposure of lungs to smoke.

These and other objects of the invention which will hereinafter become more readily apparent have been attained by providing a method of treating vascular disorders in an animal which comprises:

administering to said animal milk collected from a bovid being maintained in a hyperimmune state, in an amount sufficient to produce antiarteriosclerotic, antiaging vascular, or by tissue sparing effects.

DESCRIPTION OF THE DRAWINGS

A more complete appreciation of the invention and many of the attendant advantages thereof will be readily obtained as the same becomes better understood by reference to the following detailed description when considered in connection with the accompanying drawings; wherein:

FIG. 1 shows photomicrographs of cryostat sections of rabbit aortae stained with Oil Red 0 to specifically demonstrate lipids. x300;

A. Control rabbits: Numerous, small lipid droplets (arrows) are present;

B. Hyperimmune milk-fed rabbits: Lipid droplets are absent in the aortas's wall. The lipid (arrow) in the tissue outside the aorta is normal and illustrates that lipids would be visible if they were present in the wall of the aorta.

FIG. 2 shows scanning electron micrographs of inner ventricular surfaces of rabbit hearts. x1750;

A. Control: Two thrombi lie below the eroded epithelium of the endocardium.

B. Hyperimmune milk: The epithelium is intact and there is no evidence of thrombi.

FIG. 3 shows transmission electron micrographs of blood vessels in rabbit hearts. x3420;

A. Control: Lipid vacuoles are present in the endothelial cells (upper arrows) and smooth muscle cells (lower arrows);

B. Hyperimmune milk: Lipid vacuoles are absent in the endothelium and smooth muscle cells.

FIG. 4 is an electromicrograph (SEM) of the alveolar wall of a lung of a rat exposed to cigarette smoke for three months. x5750.

A. Control: Debris (arrows) is present on the alveolar wall and the wall is cracked, exposing a red blood cell (RBC).

B. Hyperimmune milk: The dust cell (DC) or macrophage in the center of the micrograph engulfs debris which helps to clear the alveolar wall of particles carried to the lower respiratory track in the smoke.

DETAILED DESCRIPTION OF THE PREFERRED EMBODIMENTS

The invention comprises a natural food product (milk) which has beneficial properties towards animal vascular and pulmonary systems, as well as a method for producing the same. The milk of the present invention, being a natural product, can be used to treat vascular disorders associated with any disease or injury, pulmonary disorders associated with smoking or a natural condition such as vascular aging in animals and humans without fear of side effects.

Examples of vascular disorders which may be treated with the milk of the present invention include aging disorders such as a decrease in the rigidity of vessels, and a decrease in the incidence wherein the large arteries become dilated and elongated, as well as a decrease in aneurisms which form in areas of encroaching arteriosclerotic plaques. Other aging-induced vascular damage which can be prevented or reversed with the milk of the present invention is the increase in the thickness of the arterial intima, the reversal of gradual accumulation of smooth muscle cells, as well as a decrease in the accumulation of lipid content in the arterial wall.

Among the abnormal (i.e. non-aging induced) disorders of the vascular system which are treatable (preventable or reversable) with the milk of the present invention is arteriosclerosis, which includes both atheromatous forms and non-atheromatous forms. Among the non-atheromatous forms of arteriosclerosis treatable with the milk of the present invention is focal calcification (also called Monckeberg's sclerosis), which is common in the lower extremities, upper extremities, and the arterial supply of the genital tract in both sexes. Another disorder is focal calcification, which involves degeneration of smooth muscle cells followed by calcium deposition. Another non-atheromatous form of arteriosclerosis is arteriolosclerosis which involves hyaline and general changes affecting both the intima and media of small arteries and arterioles, particularly in the spleen, pancreas, adrenal and kidney.

Importantly, the milk of the present invention can be utilized for the treatment of atherosclerosis. This involves both the prevention and regression of the formation of fatty streaks, fibrous plaques and complicated lesions, as described previously. Although it is probable that irreversible risk factors for atherosclerosis, such as male sex or genetic traits (e.g. positive family history of premature atherosclerosis) might not be reversed with the milk of the invention, the so-called reversible factors, however, may.

Thus, the milk of the invention is useful in reducing the accumulation of lipids and preventing or reversing hypercholesrerolemia or hypertriglyceridemia. Various forms of atherosclerosis can be treated.

Additionally, the milk of the invention can be utilized to reverse some of the harmful effects of smoking on lung tissue, or at least spare that and related tissues from the harmful effects and disorders associated with smoking, including a reduction in the number of macrophages present and a reduction of their activity, or phagocytosis, increasing numbers of neutrophils and lymphocytes present in lung tissue and the harmful secretions therefrom, and a increase in the thickness of the blood-air barrier, and possibly associated short windedness.

In the process of this invention, the source bovid include any milk-producing member of the genus Bos, preferably cows.

The invention is based on the discovery that when such bovid is brought to a specific state of immunization by means of periodic booster administrations of an antigen or a mixture of antigens, the bovid will produce milk which has highly beneficial properties in the treatment of vascular disorders. The beneficial milk properties are not produced by all bovids that are immunized. The induction of immune sensitivity alone is insufficient to cause the appearance of the properties in milk, as is shown by the fact that normal cow's milk does not contain these properties, even though cows have become sensitized against various antigens during normal immunization against cow diseases.

Furthermore, the properties are not always present in milk produced by bovids maintained in the immune state by booster injections. It is only in a specific hyperimmune state that the milk has the desired effects. This special state is only achieved by administering periodic boosters with sufficiently high doses of antigens or mixtures of antigens. The preferred dose range should be equal to or greater than 50% of the dosage necessary to cause primary sensitization of the bovid. Thus, there is a booster dosage threshold below which the properties are not produced in the milk even though the cow may be in what is normally called an immune state. In order to achieve the hyperimmune state it is essential to test the bovid's milk after a first series of booster administrations. If the milk does nor contain the desired properties, a second series of boosters of higher dosage has to be administered. This process is repeated until the properties appear in the milk.

In summary the process comprises the following steps:
1. Antigen selection.
2. Sensitization of the bovid by primary immunization.
3. Testing the serum of the bovid to confirm sensitivity induction.
4. Administering boosters of appropriate dosage to induce and maintain a hyperimmune state.
5. Testing anti aging or anti arteriosclerotic properties of milk.
6. Collecting milk from the bovid during the hyperimmune state.

Step 1 - Any antigens or combination of antigens may be employed. The antigens can be bacterial, viral, cellular, or any other substances to which the immune system of a bovid will respond. The critical point in Step 1 is that the antigen must be capable of inducing a state of immune sensitivity in the cow. The antigen can be administered by any method which causes sensitization. Preferably polyvalent antigens, such as bacteria, are used.

Step 2 - The preferred method of immunization is by intramuscular injection. However, other methods such as intravenous injection, intraperineal injection, oral administration, rectal suppository, etc., can be used, providing the dose is sufficient to induce sensitivity. The dosage is normally $1 \times 10^6$ cells to $1 \times 10^{20}$ cells, preferably $10^8$ cells to $10^{10}$ cells, most preferably $2 \times 10^8$ cells.

Step 3 is to determine whether or not the cow has become sensitive to the antigen. There are a number of methods known to those skilled in the art of immunology to test for sensitivity, (Methods in Immunology and ImmunoChemistry, William, C. A., Chase, W. M. Academic Press, N.Y., London (vols 1–5) (1977)). Examples of these include skin sensitivity tests, serum tests for the presence of antibodies to the stimulating antigens, and tests designed to evaluate the ability of immune cells from the host to respond to the antigen. The type of test employed will depend to a large extent on the nature of the antigen used. The preferred method is to use a polyvalent vaccine consisting of multiple bacterial species as the antigen and to test for the presence of agglutinating antibodies in the serum of the cow before and after challenge with the vaccine. The appearance of milk antibodies after immunization with the vaccine is indicative of sensitivity, and at this point, it is possible to proceed to Step 4. The minimum dose of antigen necessary to induce sensitivity depends on the type of antigen used.

Step 4 involves the induction and maintenance of the hyperimmune state. Once a bovid has been shown to be sensitized, this state is induced by repeated booster administrations of an appropriate dosage at fixed time intervals. The spacing of the administration depends on the nature of the antigen. A two-week booster interval is optimal for polyvalent bacterial antigens. Moreover, the booster administrations must not induce a state of immune tolerance. This will cause the animal to pass from a hyperimmune state to a state of immune tolerance to the antigen in which case the animal will cease to produce milk with the beneficial properties.

It might also be possible, for example, to use a combination of different immunization procedures, i.e., intramuscular injection for primary immunization and intravenous injection for booster injections, etc. Many different combinations of immunization methods might be employed by those skilled in the art to: (1) sensitize and (2) induce the hyperimmune state.

Step 5 is to test the vascular and/or pulmonary disorder treatment properties of the milk. A battery of research techniques can used to test the effects of the hyperimmune milk on the vascular and pulmonary systems of animals, preferably, rabbit or rat tissue can be used as the test tissue. These tests include in all cases feeding a rabbit or rat a diet which comprises hyperimmune milk (with a control comprising rabbits in a diet with normal milk.) After a predetermined period of time, the animals are sacrificed and their vascular or pulmonary system can be examined by any of the following techniques: Scanning electron microscopy of the endocardial surface of the heart or lungs bronchii and alocoli searching for endothelial damage or the presence of debris, respectively; transmission electron microscopy of vessels searching for lipid droplets, endothelial degeneration, lipid presence in foam cells, or tendency of fibrin or platelets to adhere to the luminal surface of endothelial cells; histological analyses of hearts searching for lipids, e.g. demonstration of lipids with oil-soluble dyes such as Oil Red or Sudan Black in sections of frozen tissue, or presence of enzymes, especially cytochrome oxidase or of lung tissue for evidence of phagocytosis; as well as histological examination of lung tissue for neutraphil and leukocyte infiltration.

Step 6 involves collection and processing of the milk. The milk can be collected by conventional methods; however, special processing is necessary to protect the beneficial properties of the milk. The beneficial properties of the milk are heat sensitive. Accordingly, low temperature pasteurization is preferred. The pasteurization temperature should not exceed 160° F for 15 seconds. Following pasteurization, the fat is removed by standard procedures and the milk is spray dried. Conventional spray-drying procedures are used, with the exception that the milk is concentrated under vacuum at low temperature so as not to destroy the beneficial properties. (See e.g. Kosikowski, F., "Cheese and Fermented Milk Products," 2d Ed, 1977). The final product is a milk powder which has beneficial properties.

Fluid milk can also be used, as well as concentrated milk products or a fraction of the milk containing the biologically active factor or factors such as the acid whey fraction.

The invention is based in part on the discovery that the milk from a hyperimmune bovid has beneficial properties on the cardiovascular system. For example, it has been discovered that in hearts of female rabbits which have been fed a steady diet of hyperimmune milk, the endothelial cells of the heart were protected against extensive endothelial damage of varying extent and severity observed in rabbits fed normal milk. In the latter rabbits, craters or holes were present where one or more cells had degenerated and detached, whereas in hyperimmune milk fed rabbits these were not present. Transmission electron microscopy of both populations of rabbits showed major differences in the blood vessels. Significant pathological features of blood vessels in control hearts included large lipid droplets, endothelial degeneration, multiple small lipid vacuoles, single or multiple large lipid droplets filling the cytoplasm of endothelial cells, foam cells latent with lipid, and a strong tendency of fibrin platelets to adhere to the luminal surface of endothelial cells. All of the aforementioned derangements accompany the pathogeneses of atherosclerosis. These derangements were not found in blood vessels from representative areas of rabbit populations which were on a steady diet of hyperimmune milk. Histological sections of hearts from the rabbits fed the hyperimmune milk and of rabbits fed control milk showed that lipid was present in the lumina of some blood vessels of control hearts and cardiac muscle fibers of control hearts were filled with lipid. Coronary blood vessels from rabbits on hyperimmune milk lacked the atherosclerotic lipid deposits which are observed in control vessels.

These results show conclusively that hyperimmune milk slows and/or represses the pathogeneses of arteriosclerosis and aging of the heart.

The same tests of rabbit populations, as well as clinical trials with human subjects, has conclusively demonstrated that diets incorporating the hyperimmune milk of this invention results in a reduction of serum cholesterol levels, as well as marked reductions in triglyceride levels and low density lipid levels, all of which are key risk factors associated with cardiovascular disease.

The invention is also based, in part, on the discovery that the milk from a hyperimmune bovid has beneficial properties on the pulmonary system of animals exposed to smoke, and particularly a sparing effect on the lung tissue thereof. For example, it has been discovered that in the lungs of rats which have been fed a steady diet of hyperimmune milk and exposed to cigarette smoke, the number of neutrophils and lymphocytes infiltrating the lungs upon exposure to smoke are substantially reduced as compared with control groups. Also, the surface of the alveoli is "cleaner" in rats receiving the hyperimmune milk and exposed to smoke then rats exposed to smoke only or smoke plus control or normal milk. The hyperimmune milk appeared to increase the activity of the dust cells or lung macrophages. The dust cells in the bronchioles and alveoli of rats fed a diet of hyperimmune milk were more active in the phagocytosis of smoke-associated debris in lungs of rats exposed to smoke than of those rats exposed to smoke only or smoke plus a diet of non-hyperimmune milk. The blood-air barrier was also observed to be thinner in rats exposed to smoke and fed a diet of hyperimmune milk than rats exposed to smoke only or rats exposed to smoke and fed normal or controlled milk.

In addition to cardiovascular tissue, 16 other tissues representing one or more components of each major organ system have also been studied from the same animals. Hyperimmune milk has no adverse effects on any of these tissues.

The milk of the invention can be provided in any amount which effects or maintains the reversal of vascular disorders or smoking associated pulmonary disorders in warm-blooded animals. Daily amounts of 1 ml to 10 liters based on fluid milk can be provided, depending on the particular circumstance of the disorder and the animal species.

The same amounts can be utilized in normal subjects when operating in a preventive mode.

In a preferred mode the milk is administered periodically (e.g. daily in dosages of approximately 40 g) for a prolonged period of time such as at least 15-30 days and more, up to several years. As will be recognized, the treatment duration can be shortened by increasing daily dosages. Additionally, smaller dosages spread out throughout the day may be more effective than a single dosage taken once a day.

The fat-free milk can be incorporated into any food product, as long as the food product is not treated at a temperature which is too elevated and would inactivate the vascular treatment properties of the product. A temperature lower than 150° C. is preferred. For example puddings or yogurt may be prepared with hyperimmune milk.

Further, it has been found that the whey fraction contains the agent or agents responsible for the beneficial properties observed and referred to above. This acid whey fraction may also be added to syrups, ice-cream mixes, candy, beverages, cattle feeds or the like. (See Kosikowski, Supra, p 446). Those of ordinary skill in the art, knowing that the whey fraction contains the factors of importance, would clearly recognize that further separation can be made to obtain more potent fractions.

Further, where alleviating disorders associated with smoking, the milk may be incorporated in the substance being smoked, such as by spraying tobacco with an aerosol form of the milk.

Having now generally described this invention, the same will be further described by reference to certain specific examples which are provided herein for purposes of illustration only and are not intended to be limiting unless otherwise specified.

PREPARATION OF MILKS

EXAMPLE 1

Five Holstein cows were immunized against Escherichia coli (American Type Culture Strain No. 13076). The primary immunization was accomplished by intramuscular injection of a vaccine containing heat-killed E. coli cells suspended in physiological saline. The concentration of bacterial cells was $4 \times 10^8$/cc. A dose of 5 cc ($20 \times 10^8$) cells was injected i.m. once weekly for four consecutive weeks. Milk collected during the fifth week was tested for the presence of antibodies against E. coli. The presence of antibody against E. coli was determined using a micro-agglutination procedure. This procedure involves reacting different dilutions of milk whey with a fixed concentration of E. coli bacterial cells suspended in buffer. The presence of antibodies in the milk causes agglutination of the bacterial cells. The milk is diluted in a serial fashion and there comes a point when the concentration of antibodies is too low to cause the agglutination reaction. The maximum dilution which causes agglutination is the antibody titer. The presence of high antibody concentration in milk is an indication that the immunization procedure causes sensitization of the cow's immune system against the antigen. Table 1 compares the antibody titer against E. coli in the five cows before and after primary immunization.

TABLE 1

| Cow No. | Milk Antibody Titer in 5 Cows Before and After Immunization Against E. coli | |
|---|---|---|
| | Before Immunization | After Immunization |
| 1 | 0 | 640 |
| 2 | 0 | 1,280 |
| 3 | 0 | 5,000 |
| 4 | 0 | 1,280 |
| 5 | 0 | 10,000 |

In each case there was a significant increase in the milk titer against E. coli following immunization. From this it was concluded that the immunization caused sensitization of the cow against the E. coli. Having induced a state of sensitivity, the cows were given booster injections of the same dose of antigen every 14 days, thus establishing and maintaining a period of hyperimmune state during which time the milk was collected daily and processed to obtain skimmed powdered milk.

The skimmed powdered milk induced by the method outlined above was tested for beneficial properties using a number of tests, infra.

EXAMPLE 2

The identical experiment as described in Example 1 was undertaken with the exception that a polyvalent vaccine comprised of the bacterial strains listed below in Table 2 was used as the selected antigen. The different bacterial strains were combined by mixing equal weights of the lyophilized bacterial cells and diluting the mixture in saline to obtain a concentration identical to that used in Example 1. Results of the tests on milk produced using these selected antigens were positive, infra.

TABLE 2

| Bacterial Antigens | |
|---|---|
| Organism | ATTC No. |
| Staphylococcus aureus | 11,631 |
| Staphylococcus epidermidis | 155 |
| Streptococcus pyogenes, A. Type 1 | 8,671 |
| Streptococcus pyogenes, A. Type 3 | 10,389 |
| Streptococcus pyogenes, A. Type 5 | 12,347 |
| Streptococcus pyogenes, A. Type 8 | 12,389 |
| Streptococcus pyogenes, A. Type 12 | 11,434 |
| Streptococcus pyogenes, A. Type 14 | 12,972 |
| Streptococcus pyogenes, A. Type 18 | 12,357 |

TABLE 2-continued

| Bacterial Antigens | |
|---|---|
| Organism | ATTC No. |
| Streptococcus pyogenes, A. Type 22 | 10,403 |
| Aerobacter aerogenes | 884 |
| Escherichia coli | 26 |
| Salmonella enteritidis | 13,076 |
| Pseudomonas aeruginosa | 7,700 |
| Klebsiella pneumoniae | 9,590 |
| Salmonella typhimurium | 13,311 |
| Haemophilus influenzae | 9,333 |
| Streptococcus viridans | 6,249 |
| Proteus vulgaris | 13,315 |
| Shigella dysenteriae | 11,835 |
| Streptococcus, Group B | |
| Diplococcus pneumoniae | |
| Streptococcus mutans | |
| Corynebacterium, Acne, Types 1 and 2 | |

*American Type Culture Collection 12301 Parklawn Drive Rockville, Maryland 20852

It should be noted here that the milk produced in this Example is identical to that produced in a preferred embodiment of the invention disclosed in copending U.S. application Ser. No. 875,140, filed February 6, 1978 by Beck and in U.S. Pat. No. 4,284,623. The application discloses that the milk of the present Example also has highly beneficial anti-arthritic properties, and the patent discloses that the milk has anti-inflammatory properties.

EXAMPLE 3

A strain of *Streptococcus mutans* was cultured in accordance with established techniques. Cultures of *S. mutans* AHT (serological a), BHT (group b), 10449 (group c) and 6715 (group d) were grown in dialyzed tryptose medium. The cells were harvested by centrifugation at 4000×G and washed five times with 0.1 M phosphate buffered saline, pH 7.0. The cells were inactivated by heating at 60° C for 30 minutes and resuspended to a final concentration of *S. mutans* AHT, BHT, 10449 and 6715 at $5 \times 10^8$ cells/ml. This preparation was used to immunize two cows. Each cow was immunized on two separate occasions with fresh antigen from all four groups of *S. mutans* (groups a, b, c and d). A cow was then immunized in accordance with the established techniques of this invention to generate a milk product. Following immunization, blood samples of the cow were taken until the serum antibody titer reached its highest level, then the milk was collected. The milk itself was then dried and powdered, again in accordance with established techniques, to produce a powdered milk having positive beneficial effects.

It should be noted here that the milk produced in this Example is identical to the caries-inhibiting milk disclosed by Beck in B.P. 1,505,513.

Example 4

The polyvalent vaccine shown below in Table 3 was utilized as in Example 2 to immunize a cow and obtain hyperimmune milk with cardiovascular or pulmonary effects.

TABLE 3

| | Bacteria | ATTC No. |
|---|---|---|
| 1. | Pseudomonas aeruginosa | 14212 |
| 2. | Pseudomonas maltophiia | 17666 |
| 3. | Streprococcus equisimili | 9542 |
| 4. | Streptococcus dysgalactiae | 27957 |
| 5. | Streptococcus uberis | 27958 |
| 6. | Streptococcus bovis | 15351 |
| 7. | Streptococcus bovis | 27960 |
| 8. | Pasteurella multocida | 9659 |
| 9. | Pasteurella multocida | 6533 |
| 10. | Pasteurella haemolytica | 14003 |
| 11. | Pasteurella multocida | 15743 |
| 12. | Moraxella bovis | 10900 |
| 13. | Actinobacillus lignieresi | 13372 |
| 14. | Corynebacterium renale | 10848 |
| 15. | Fusobacterium necrophorum | 25286 |
| 16. | Bacillus cereus | 25621 |
| 17. | Salmonella dublin | 15480 |
| 18. | Salmonella heidleberg | 8326 |
| 19. | Salmonella paratyphi | 11511 |
| 20. | Yersinia enterocolitica | 9610 |

BIOLOGICAL STUDIES

A Cardiovascular Effects

Materials and Methods 1. Animals

Nine, young adult female rabbits of the New Zealand White strain were used for this study. Rabbits were housed in the College of Medicine's Vivarium at the University of South Alabama in Mobile. Th ®room in which the rabbits were kept was maintained at 72° F. with 12 hours of light followed by 12 hours of darkness during each 24 hr. period. Only one rabbit was housed in each cage.

The rabbits were fed the diets (below) and sacrificed during the second and third weeks after end of the diets.

2. Diets

The rabbits were divided into two groups. Both groups received a balanced laboratory chow *ad libitum*. Control rabbits in Group I (N=4) received Jerrell's nonfat dry milk dissolved in tap water (15 dry milk/500 ml water). Experimental rabbits in Group II (N=5) received the same concentration of dry hyperimmune milk from either Examples 1, 2, 3 or 4 which was also dissolved in tap water. The water-milk mixture was changed daily. The fresh mixture was placed in sterilized glass or plastic bottles. Rabbits received no liquid other than the water used to dissolve the dry milk. 3. Methods of Study After 3 months of drinking the dissolved, non-fat dry milk (Group I) or the hyperimmune milk rabbits were weighed and anaesthetized by injecting sodium pentabarbital into an ear Vein. The body weight of each rabbit at the time of sacrifice was compared to its body weight on the first day of the diet. There was no significant difference between the body weights to rabbits receiving hyperimmune milk and those receiving the non-fat dry milk. Hearts and the great vessels at the base of the heart were removed and prepared for study by several different procedures. Specimens were coded so that the investigator was unaware whether the material was control or experimental.

Results and Comments

1. Scanning Electron Microscopy

For SEM, the inner (endocardial) surface of the heart was scanned using variable magnifications (X10-40,000). Areas of specific interest minimum of 5 randomly selected areas/heart) were then studied and photographed.

Control hearts, in contrast to experimental hearts, showed extensive endothelial damage that varied in extent and severity. Craters or holes were present where one or more cells had degenerated and detached. Small holes were present in many cells. In some instances, a fibrin-like substance mixed with blood cells and platelets was around or within the craters. Such sites were interpreted as stages in the formation of atheromatous thrombi.

Loss of endothelial cells as evident in the control hearts would expose blood in the heart chambers to endocardial connective tissue and lead to the formation of thrombi. SEM showed that hyperimmune milk protected rabbit endothelial cells and prevented thrombogenesis.

2. Transmission Electron Microscopy

TEM showed major differences in the blood vessels of control and experimental hearts. Significant pathological features of blood vessels in control hearts included: (1) large lipid droplets that sometimes occluded vascular lumina; (2) endothelial degeneration; (3) multiple, small lipid vacuoles in endothelial cells; (4) single or multiple large lipid droplets that almost filled the cytoplasm of endothelial cells; (5) foam cells laden with lipid; (6) strong tendency of fibrin and platelets to adhere to the luminal surface of endothelial cells.

All of the aforementioned derrangements accompany the pathogenesis of atherosclerosis. Coronary, renal, and cerebral arteries are known to be especially susceptible to atherosclerosis. There is focal involvement of the blood vessels, rather than total involvement throughout their length. The disease was not found in blood vessels from representative areas of the hearts of rabbits who drank immune milk.

3. Histology

Portions of hearts from all control rabbits were divided; 1 part was embedded in paraffin, and 1 part in plastic. Sections of plastic specimens cut at a thickness of 1 micrometer and stained with toluidine blue or paragon clearly showed two differences between control and experimental hearts: (1) lipid was present in the lumina of some blood vessels of control hearts, and (2) some cardiac muscle fibers of control hearts were filled with lipid. Hearts from rabbits who drank immune milk did not manifest these features.

4. Demonstration of Lipids

Lipids were localized by two standard methods, Oil Red 0 and Sudan Black B. Both methods selectively demonstrate lipids in sections of frozen tissue.

Each method showed lipid deposits in the tunica intima and tunica media of blood vessels in control hearts. These two tunics of control aortas were particularly heavily infiltrated with lipid. Tunica intimas of blood vessels in control rabbits contained thickenings associated with lipid that were typical of atherosclerosis. Coronary blood vessels from rabbits on hyperimmune milk, however, lacked atherosclerotic lipid deposits.

5. Enzymes

Activities of the following enzymes were studied and evaluated in frozen sections of control and experimental rabbit hearts: (1) acid phosphatase, (2) alkaline phosphatase, (3) isocitrate dehydrogenase, (4) succinate dehydrogenase, and (5) cytochrome oxidase. The activity of acid phosphatase was also determined biochemically.

Of the several enzymes whose activities were evaluated, only cyrochrome oxidase (an enzyme associated with aging) showed significantly greater activity in control hearts than in experimental hearts. It is noteworthy that control hearts contained foci of cardiac muscle fibers, measuring about 1 mm in diameter, that stained intensely. Such areas were evidently very rich in mitochondria and may represent focal areas of aging.

6. Blood Stream Levels

Analysis of the serum cholesterol levels in the rabbits of these studies revealed a marked decrease in serum cholesterol levels. Those control rabbits fed a diet without hyperimmune milk demonstrate an average serum cholesterol level of 4,450 mg/dl. In contrast, the rabbits fed diet of hyperimmune milk exhibited a serum cholesterol level average less than half of that figure, 2,167 mg/dl. This is believed the mechanism whereby the physiological improvements discussed above are affected.

7. Clinical Studies

Clinical studies have now been initiated for three human subjects, to determine the value of the hyperimmune milk of this invention in the reduction of plasma lipid values. Although by no means complete, these studies clearly indicate the value of the hyperimmune milk diet in reducing lipid values. Although not tested against controls for obvious reasons, beginning lipid values have been markedly reduced for all three subjects. The exact lipid values are reflected in Table 4.

B. Pulmonary Effects

Pulmonary effects studies similar to those related above with regard to cardiovascular effects were performed on rats to determine the effect of a diet of hyperimmune milk on mammals exposed to cigarette smoke. The diets and method of study were substantially similar to those related above with regard to the studies on cardiovascular effects, except the subject animals were female albino rats, of the Charles Rivers, CD strain. A total of 68 rats were involved in the studies.

TABLE 4

| Plasma Lipid Values For Human Subjects | | | |
|---|---|---|---|
| | TRIG | CHOL | LDL |
| SUBJECT IF | | | |
| Beginning | 88 | 170 | 107 |
| 6 wk IM | 61 | 140 | 83 |
| SUBJECT 2F | | | |
| Beginning | 71 | 173 | 114 |
| 6 wk IM | 69 | 156 | 97 |
| 12 wk IM | 87 | 150 | 88 |
| SUBJECT 3M | | | |
| Beginning | 675 | 269 | — |
| 6 wk IM | 190 | 264 | 181 |
| 12 wk IM | 210 | 265 | 178 |

Values = mg/dl

RESULTS AND COMMENTS

Through histological study, it was determined the lungs of control rats not exposed to smoke and the lungs of rats on a hyperimmune milk diet and exposed to smoke contained far fewer neutrophils than the lungs of rats exposed to smoke or to smoke and fed a diet of normal or control milk. Lymphocytes were also fewer in number in the lungs of the control animals, and even further reduced in the bronchial-associated lymphoid tissue (BALT) in the lungs of rats that were fed a diet of hyperimmune milk and exposed to smoke.

Figure 1A:
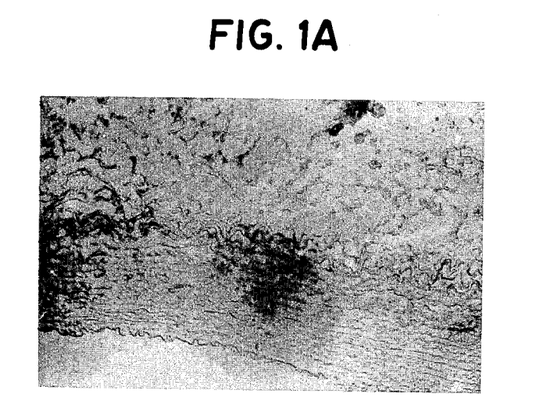
Figure 1B:
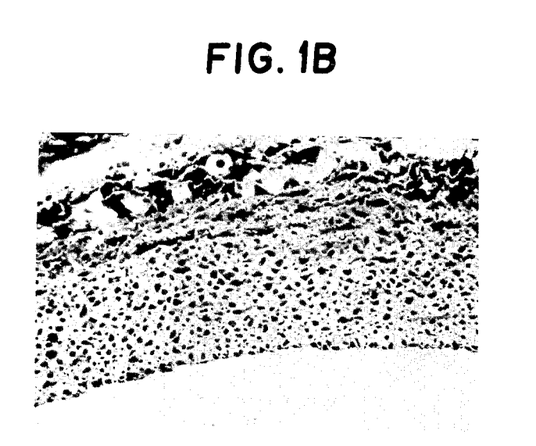
Figure 2A:
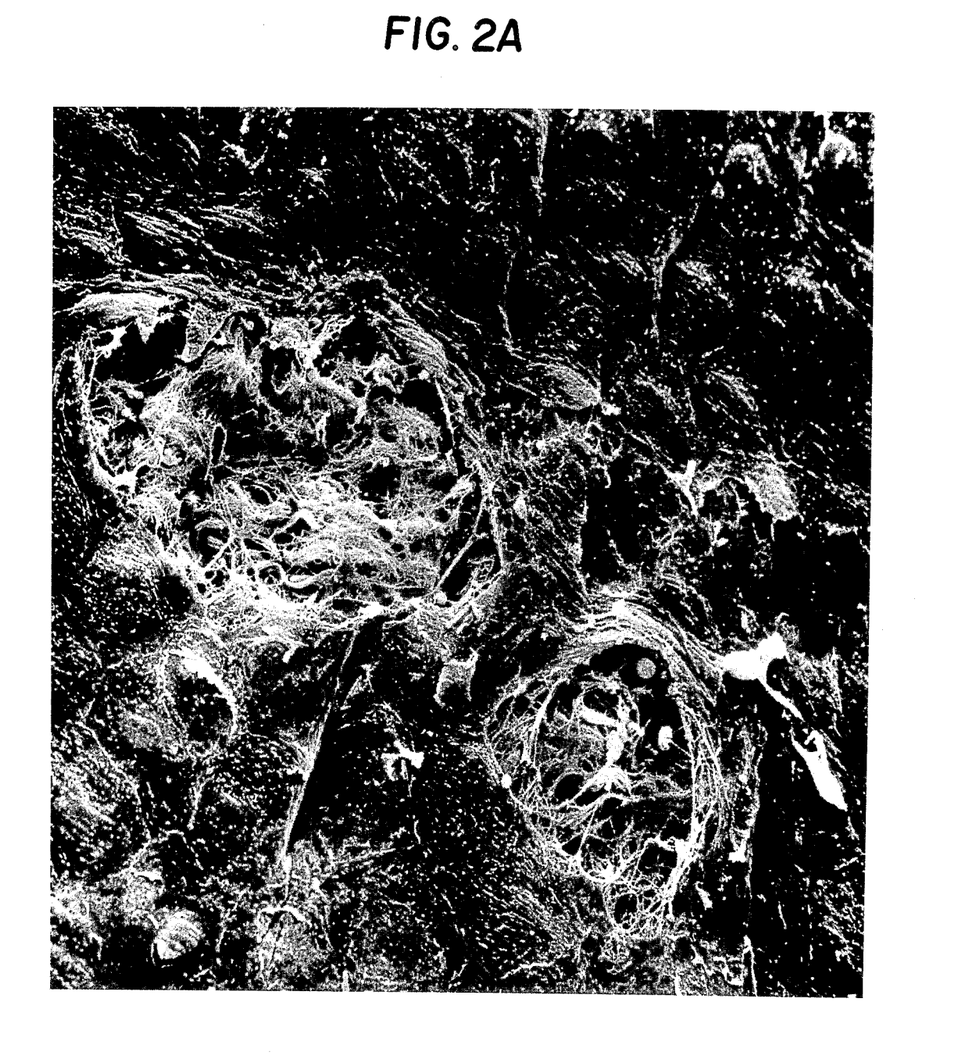
Figure 2B:
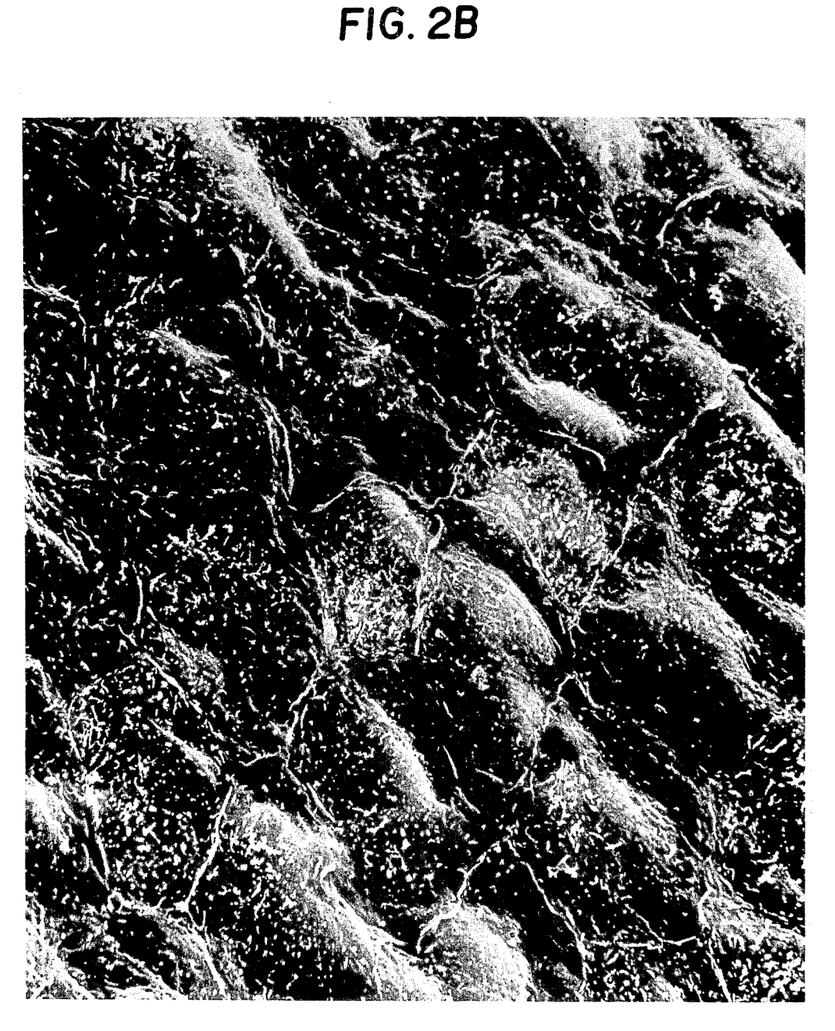
Figure 3A:
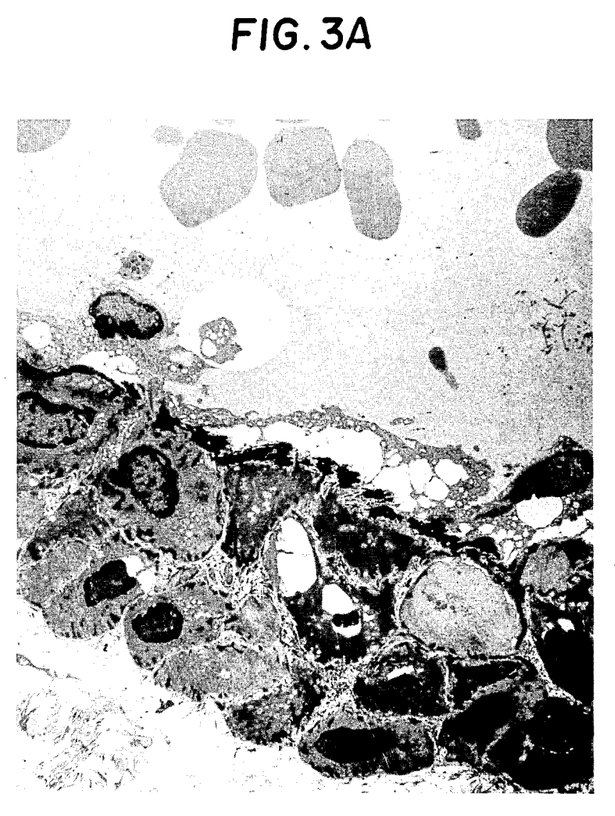
Figure 3B:
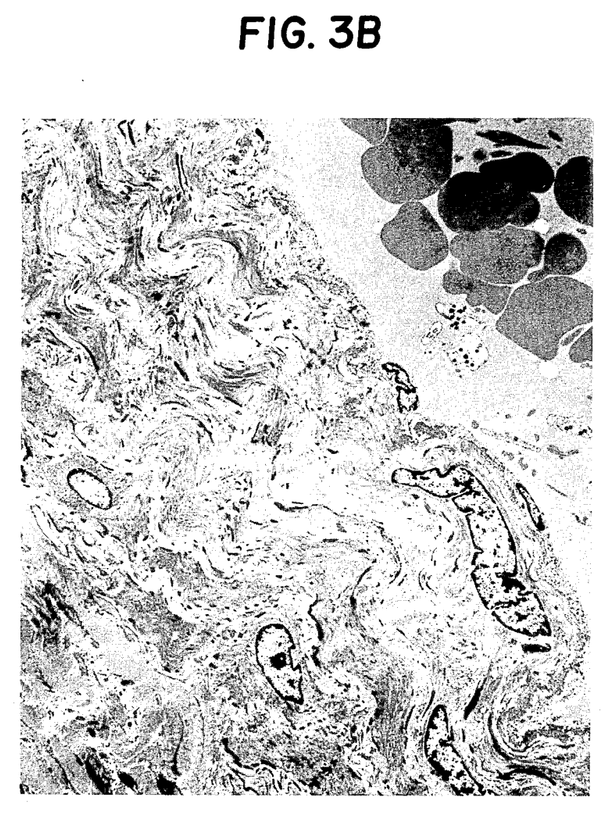
Figure 4A:
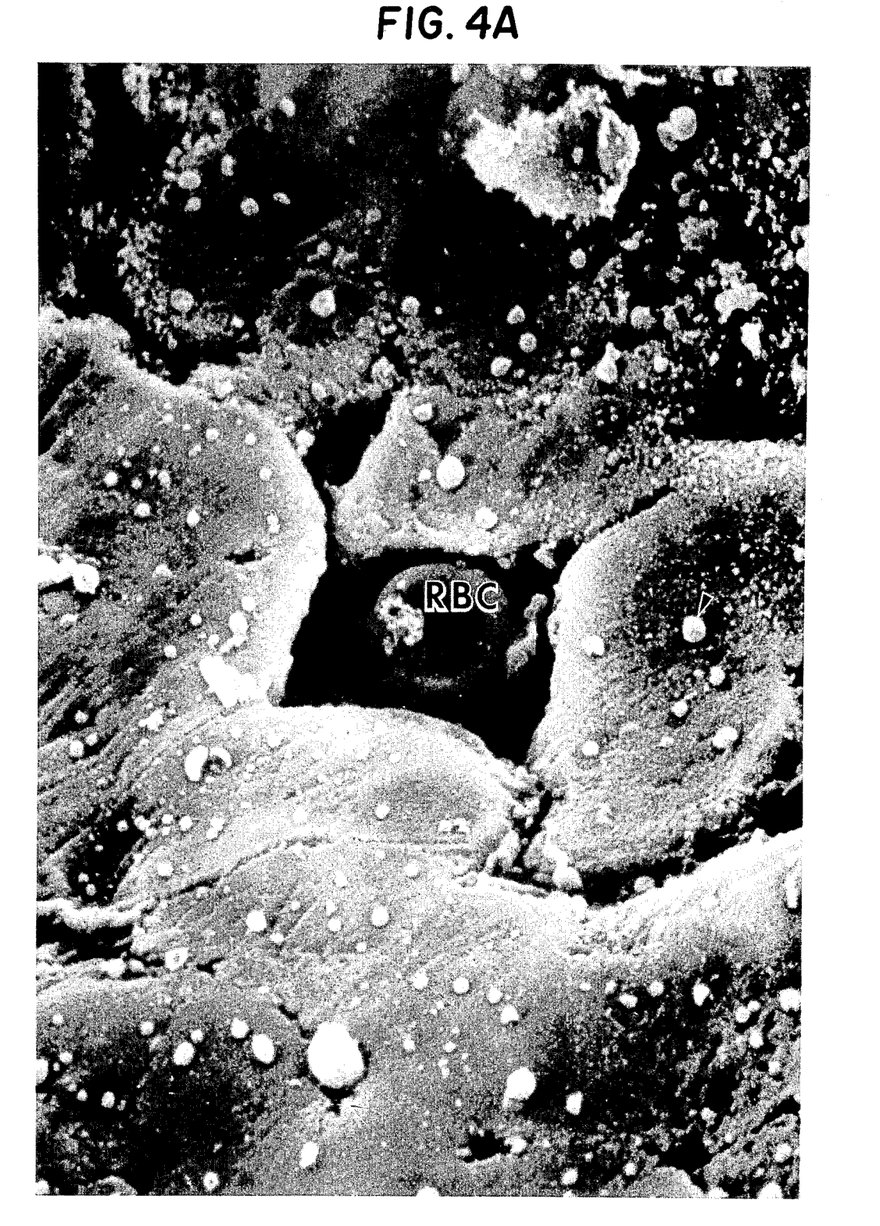
Figure 4B:
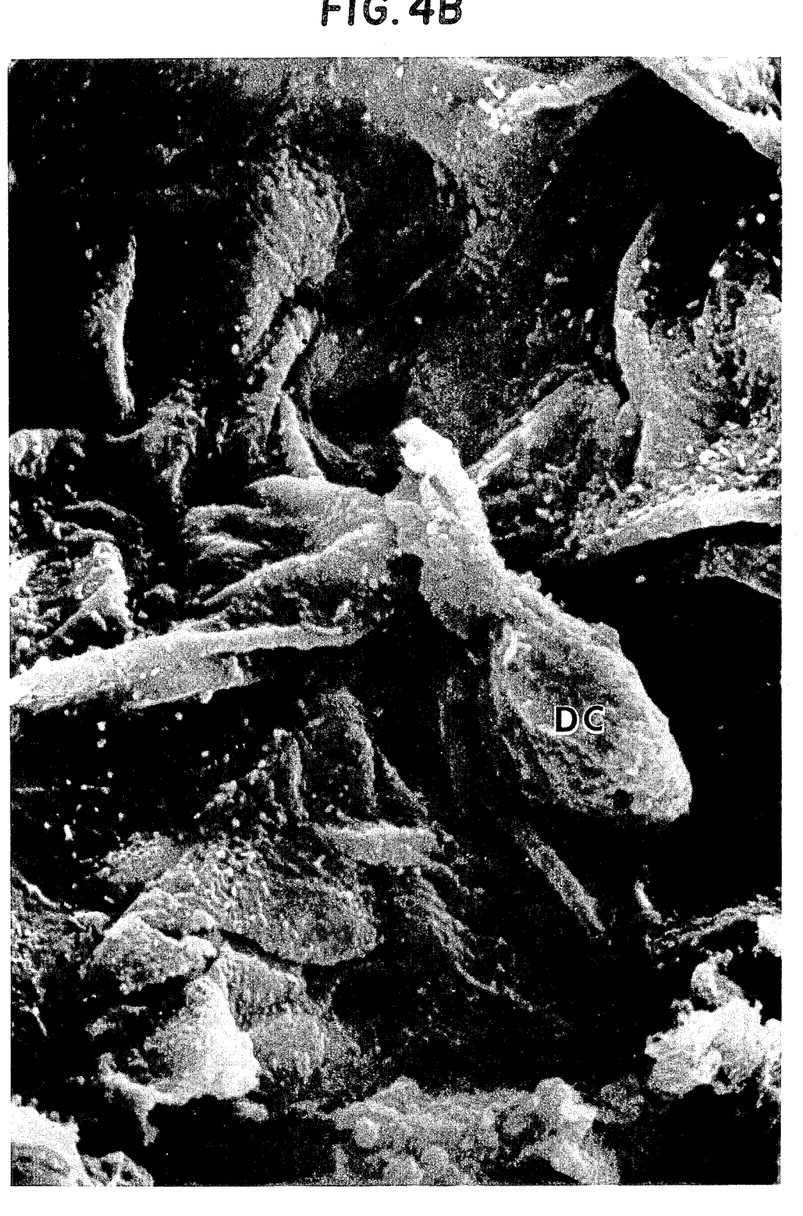
Figure 5:
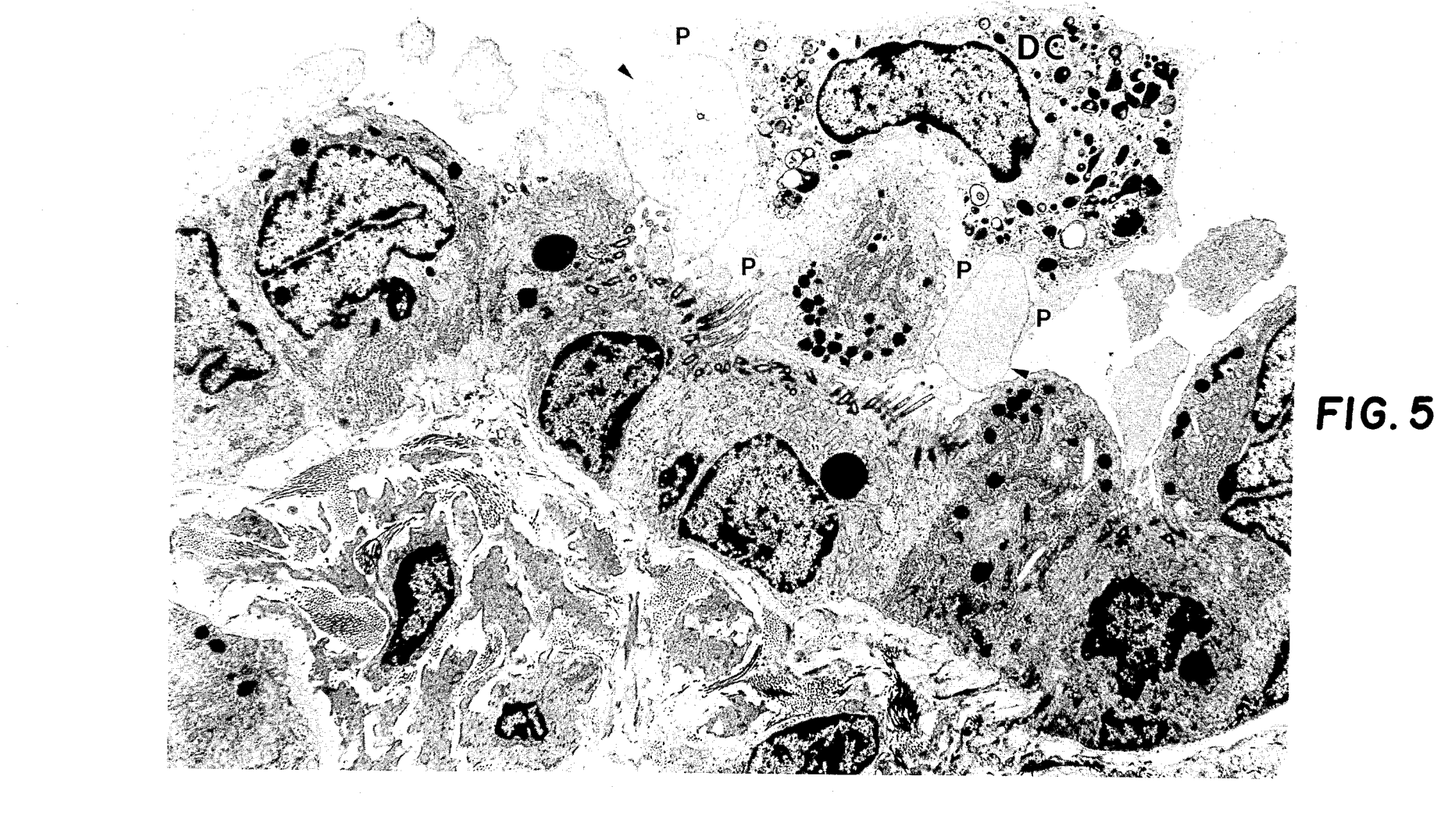
FIG. 5 is an electromicrograph (TEM) of a rat exposed to cigarette smoke for three months and receiving hyperimmune milk. x5500. Psuedopodia (P) of the dust cell (DC) have surrounded the luminal debris (arrows) in the initial stage of phagocytosis.
Figure 6:
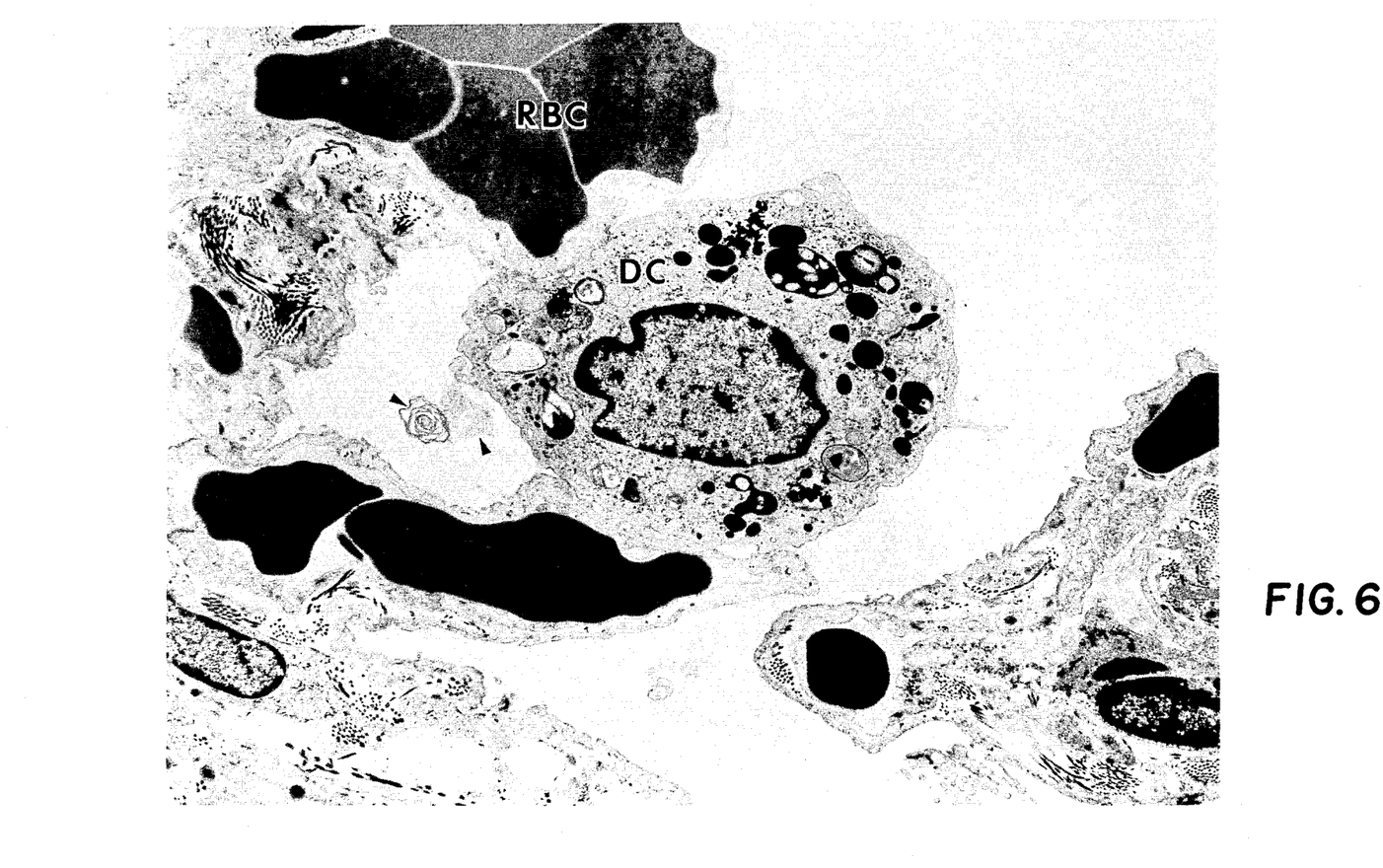
FIG. 6 is an electromicrograph (TEM) of a dust cell on a type 1 alveolar cell in a rat lung exposed to cigarette smoke for three months and receiving hyperimmune milk. x1200. The dust cell (DC) contains phagocytosed material and is involved in the uptake of debris (arrows) in the alveolar lumen. Red blood cells (RBC) occupy capillary lumina in the alveolar walls.

Scanning electron microscopy showed the surface of the alveoli of rats exposed to smoke and fed a diet of hyperimmune milk to be markedly" cleaner than those of rats exposed to smoke or exposed to smoke and fed a diet of normal or control milk. The hyperimmune milk diet appeared to increase the activity of the dust cells, or lung macrophages. The dust cells in bronchii, bronchioles and alveoli were far more active in phagocytosis in the lungs of rate exposed to the smoke and fed a diet of hyperimmune milk than after the other experimental conditions. Of the rats exposed to smoke, only those fed a hyperimmune diet exhibited dust cells consistently on the surfaces of Type 1 alveolar cells in the gas exchange passages and on the epithelial cells of the air conducting passages. Pseudopodia of dust cells engulfed products of the epithelial cells and other debris that was present (FIGS. 4-6). Thus, the physiological "patentcy" of the air-conducting and respiratory portions of the lung was maintained in rats fed hyperimmune milk, even in the presence of excessive secretion and debris associated with cigarette smoking.

The blood-air barrier was observed to be thicker in the lungs of rats exposed to smoke with or without normal or control milk than in rats exposed to smoke and fed a diet of hyperimmune milk. This phenomenon is believed to be closely associated with the short-windedness often observed in conjunction with cigarette smoking.

Having now generally described this invention it will become readily apparent to one skilled in the art that many changes and modifications can be made thereto without affecting the spirit or scope thereof.

What is new and intended to be convered by Letters Patent of the United States is:

1. A method for reducing particulate matter deposited in lungs wherein said particulate matter is associated with environmental particulates in smoke, in an animal which comprises:
   administering to said animal milk collected from a bovid being maintained in a hyperimmune state, in an amount and for time sufficient to stimulate phagocytosis of said particulate matter present in said lungs.

2. The method of claim 1, wherein said smoke comprises smoke produced by tobacco combustion.

3. The method of claim 1 wherein said milk is in powdery form.

4. The method of claim 1 wherein said milk is in fluid form.

5. The method of claim 1 wherein said milk is in concentrated form.

6. The method of claim 1 wherein said milk is incorporated into a food product.

7. The method of claim 6 wherein said product is yogurt.

8. The method of claim 1 wherein said bovid is a cow.

9. The method of claim 1 wherein said bovid is maintained in said hyperimmune state by administering to said bovid booster injections of an antigen or mixture of antigens.

10. The method of claim 9 wherein said antigen or mixture of antigens booster is injected in a dose of $10^6$ cells to $10^{20}$ cells.

11. The method of claim 1 wherein said milk is prepared by a process which comprises:
   sensitizing a bovid with an antigen or mixture of antigens;
   administering boosters of antigen of a dosage sufficient to induce and maintain a hyperimmune state in said bovid; and thereafter collecting said milk from said bovid.

12. The method of claim 11 wherein said process further comprises:
   pasteurizing said collected milk; and
   removing the fat from said milk.

13. A method of stimulating lung macrophage activity to reduce foreign particulate matter in an animal, which comprises:
   administering to said animal milk collected from a bovid being maintained in a hyperimmune state, in an amount and for a time sufficient to produce said macrophage activity increase.

* * * * *